United States Patent

Ogata et al.

[11] Patent Number: 5,911,953
[45] Date of Patent: Jun. 15, 1999

[54] APPARATUS FOR DETECTING AND ANALYZING ADSORBATES

[75] Inventors: Itsuhei Ogata, Anjo; Atsuhiro Sumiya, Hekinan; Tsukasa Satake, Ootsu, all of Japan

[73] Assignees: Nippon Soken, Inc., Nishio; Horiba, Inc., Kyoto, both of Japan

[21] Appl. No.: 08/865,484

[22] Filed: Jun. 2, 1997

[30] Foreign Application Priority Data

Jun. 14, 1996 [JP] Japan .................................. 8-154525

[51] Int. Cl.⁶ .......................... G01N 31/10; G01N 21/71
[52] U.S. Cl. ........................... 422/91; 422/88; 250/343; 250/352; 436/37; 436/134; 436/137; 436/155; 436/159; 436/181
[58] Field of Search .......................... 422/91, 83, 88; 436/37, 134, 133, 137, 147, 155, 159, 181, 183; 250/343, 352

[56] References Cited

U.S. PATENT DOCUMENTS

| 4,667,105 | 5/1987 | Miyatake et al. | 250/338 |
| 5,280,177 | 1/1994 | Bruno | 250/343 |

FOREIGN PATENT DOCUMENTS

| 4-115141 | 4/1992 | Japan . |
| 7-009060 | 3/1995 | Japan . |
| 8-15139 | 1/1996 | Japan . |
| 8-86763 | 4/1996 | Japan . |
| 9-68465 | 3/1997 | Japan . |

OTHER PUBLICATIONS

R.O. Kagel et al. *Chem. Abstr. 1967*, 67, 68975K.
D. Treibmann et al. *Jena Rev. 1980*, 25, 225–228.
H. Miura et al, *J. Phys. E. 1996*, 15, 373–377.
Q. Jiang et al, *Fenzi Cuihua* 1996, 10, 201–206.
G.A. Galkin et al. *Zh. Fiz. Khim. 1967*, 41, 740–742.
J.K. Barr *Infrared Phys. 1969*, 9, 97–108.
A. Igarashi et al. *Rev. Sci. Instrum. 1973*, 44, 321–322.
M.J. Heal et al. *J. Phys. E 1974*, 7, 352–354.
I.M. Hamadeh et al. *J. Catal. 1984*, 88, 264–272.
Z.H. Chen et al. *Bunk Kenkyu 1993*, 42, 229–235.
F.C Moates et al. *Ind. Eng. Chem. Res. 1996*, 35, 4801–4803.

*Primary Examiner*—Arlen Soderquist
*Attorney, Agent, or Firm*—Pillsbury Madison & Sutro LLP

[57] ABSTRACT

A solid object carrying a catalyzer thereon is placed in a closed reaction chamber into which test gases are supplied and is heated up to a temperature of 1000° C. Adsorbates are formed on the surface of the solid object under the test gas flow in the closed reaction chamber. Infrared radiations radiated from the adsorbates are emitted through an infrared-transmissive window hermetically formed on a wall of the closed reaction chamber, and are analyzed by an infrared radiation spectrometer and observed by a microscope. The infrared-transmissive window is cooled down by a cooling device attached thereto so that the temperature of the window does not exceed a certain level, e.g., 200° C. Thus, the adsorbates formed on the solid object can be detected and analyzed under conditions where the test gas is actually flowing and the temperature of the solid object is elevated up to a high level. Since the infrared-transmissive window is cooled down and prevented from being broken by heat, the detection and analysis of the adsorbates are performed safely.

9 Claims, 3 Drawing Sheets

APPARATUS FOR DETECTING AND ANALYZING ADSORBATES

CROSS-REFERENCE TO RELATED APPLICATION

This application is based upon and claims benefit of priority of Japanese Patent Application No. Hei-8-154525 filed on Jun. 14, 1996, the content of which is incorporated herein by reference.

BACKGROUND OF THE INVENTION

1. Field of the Invention

The present invention relates to an apparatus for detecting and analyzing adsorbates adsorbed on a solid object such as a catalyzer carrier used in a device for cleaning exhaust gas from an internal combustion engine, a deodorant carrier and the like. The apparatus is used for observing states of adsorption, detecting kinds of the adsorbates, analyzing a adsorption mechanism and evaluating the solid object.

2. Description of Related Art

To observe adsorbates adsorbed on a solid object, and to find out a reaction and adsorption mechanism, an infrared spectrometer has been used in a detection apparatus of this kind. The infrared spectrometer detects an infrared radiation peculiar to an adsorbate from an infrared spectrum of the adsorbate, and, thereby, the kind of the adsorbate is determined and the amount of the adsorbate is measured. As an infrared spectrometer, two types of the spectrometer have been used. One is a Fourier transform infrared spectrometer with diffuse reflectance equipment, and the other is a Fourier transform infrared emission spectrometer. When the former is used, there are some difficulties to detect a specific infrared radiation from an adsorbate having a temperature higher than 500° C. because a total amount of the radiation increases as the temperature becomes higher and the increased amount of the radiation acts as a noise in detection of the specific radiation, decreasing a signal-to-noise ratio.

An example of the detecting apparatus in which the latter spectrometer, i.e., the Fourier transform infrared emission spectrometer is used, is described in Japanese Patent Laid-Open Publication No. Hei-4-115141. In this apparatus, a specimen on which an adsorbate is adsorbed is prepared before observation and it is observed by the spectrometer while heating it in an open space. In this observation, the specimen and an object lens must be placed close enough to each other to receive substantially all radiations from the specimen with a good signal-to-noise ratio. In the publication, however, it is not mentioned how to realize this requirement at a temperature higher than 500° C. In addition, the specimen can be observed only at its static condition because the specimen with the adsorbate has to be prepared before observation and is heated during the observation. In other words, it cannot be observed under the condition where gases formulating the adsorbate are actually flowing. To attain valuable results from the observation and analysis, it is necessary to observe and analyze the adsorbate under the condition where gases are actually flowing.

In order to realize a dynamic observation and analysis, it is considered to place the solid object on which the adsorbate is to be formed in a closed chamber and to make a gas flow in the chamber, and to observe and analyze infrared radiations from the adsorbate through an infrared-transmissive window disposed on a wall of the closed chamber. In this arrangement, it is necessary to place the infrared-transmissive window between an object lens for receiving the infrared radiations and the solid object having a high temperature. The window may be broken by heat from the hot solid object at a high temperature and the gas in the closed chamber may leak to the outside, thereby endangering a safe operation of the observation and analysis.

SUMMARY OF THE INVENTION

The present invention has been made in view of the above-mentioned problems, and an object of the present invention is to provide an apparatus for safely detecting and analyzing adsorbates under a dynamic condition where gases forming adsorbates are actually flowing, more particularly to provide an apparatus in which a solid object is placed and heated in a closed reaction chamber into which test gases flow, infrared radiations from adsorbates formed on the solid object are radiated through an infrared-transmissive window, and the adsorbates are detected and analyzed by a spectrometer, thereby achieving the detection and analysis at an elevated temperature, e.g., up to 1000° C.

The infrared radiations from the solid object having a high temperature up to 1000° C. must be observed and analyzed by a spectrometer. The infrared-transmissive window has to be placed sufficiently close to the hot solid object in order to receive a substantial portion of the radiations therefrom. Therefore, the window is heated up to a high temperature, which may cause breakage of the window. According to the present invention, the infrared-transmissive window is cooled down by a cooling device attached thereto so that the temperature of the window does not exceed a certain level, e.g., 200° C. The window is protected from the heat radiations from the hot solid object and a furnace for heating the solid object, and, thereby, the testing is performed safely under a high temperature.

A gas detector may be used for detecting gas leakage from the closed reaction chamber and for alarming the leakage in order to further enhance a safe operation of the detecting and analyzing apparatus. Further, a test gas supply controller may be also used in the apparatus so that the test gas supply to the closed reaction chamber is shut down in case the gas leakage from the reaction chamber is found by the gas detector.

The infrared radiations coming through the infrared-transmissive window are fed into an optical device and analyzed by an infrared radiation spectrometer, and the results of the analyses are observed by a microscope attached to the optical device and the spectrometer. The solid object on which the adsorbates are formed by the test gas can be evaluated through the observation and analysis of the adsorbates.

Other objects and features of the present invention will become more readily apparent from a better understanding of the preferred embodiment described below with reference to the following drawings.

DETAILED DESCRIPTION OF THE PREFERRED EMBODIMENT

Figure 1:
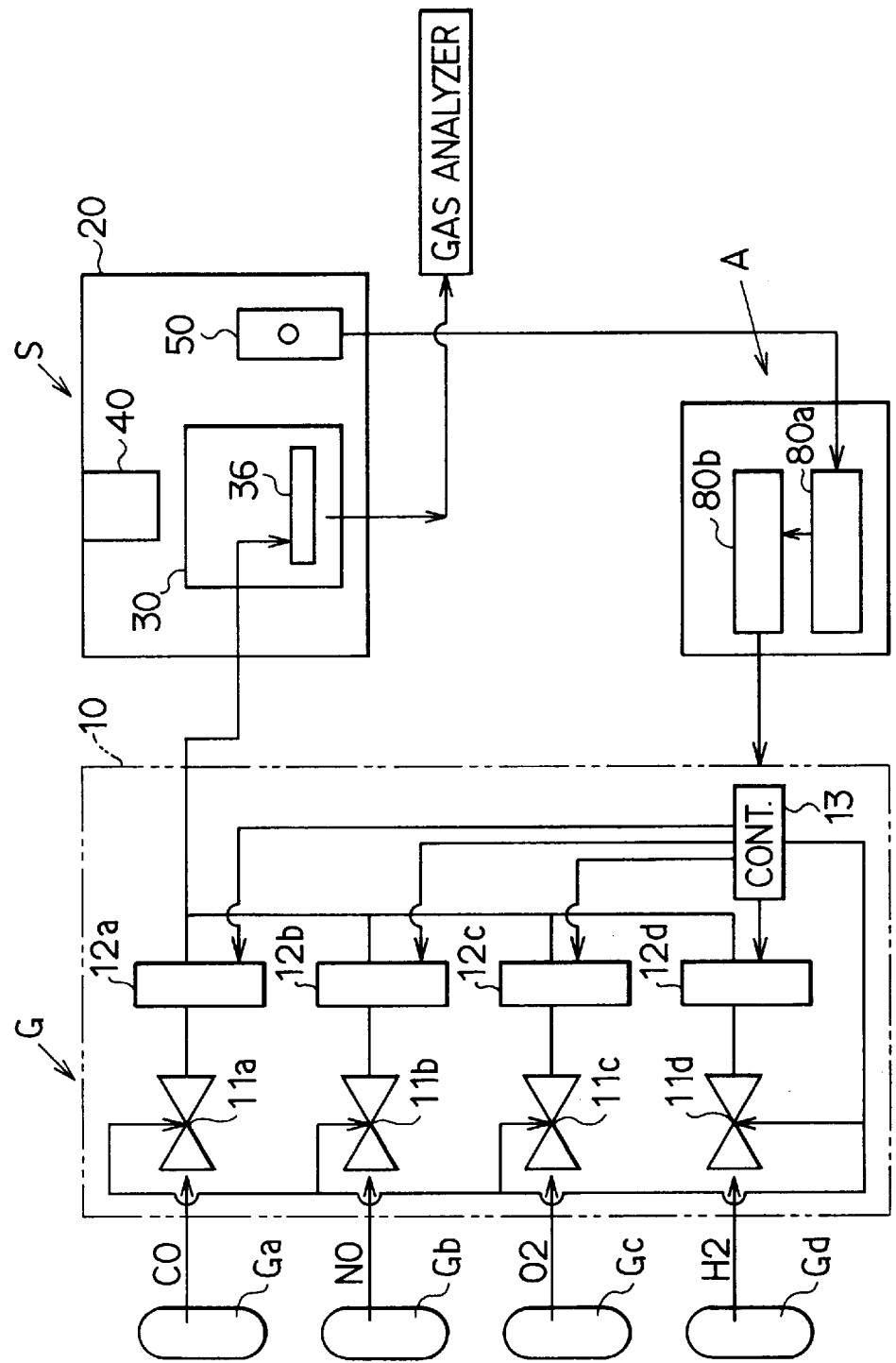
FIG. 1 shows a whole system for detecting and analyzing adsorbates on a solid object according to the present invention.
Figure 2:
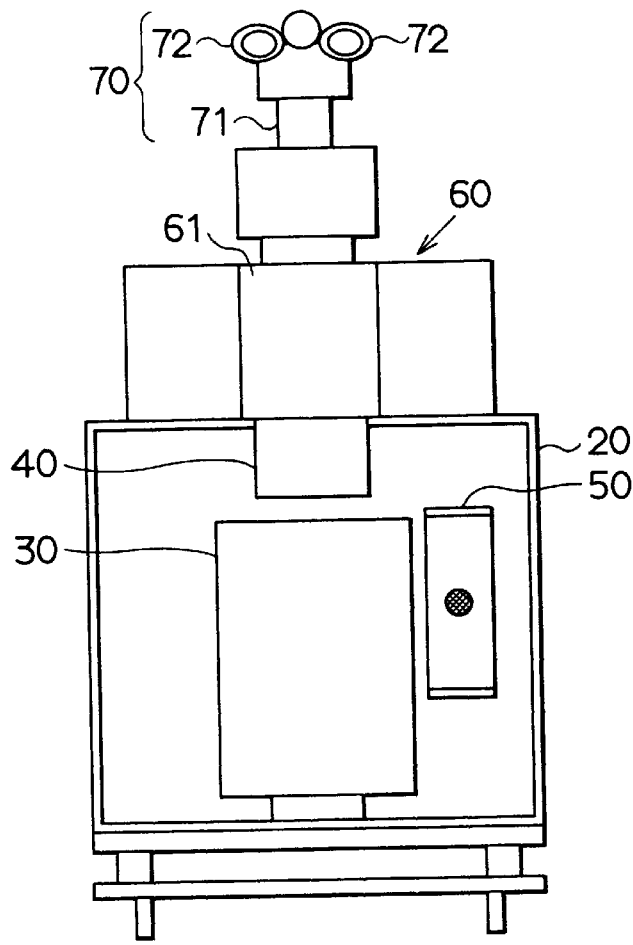
FIG. 2 is a partially enlarged view of FIG. 1, showing an apparatus for detecting and analyzing adsorbates according to the present invention.
Figure 3:
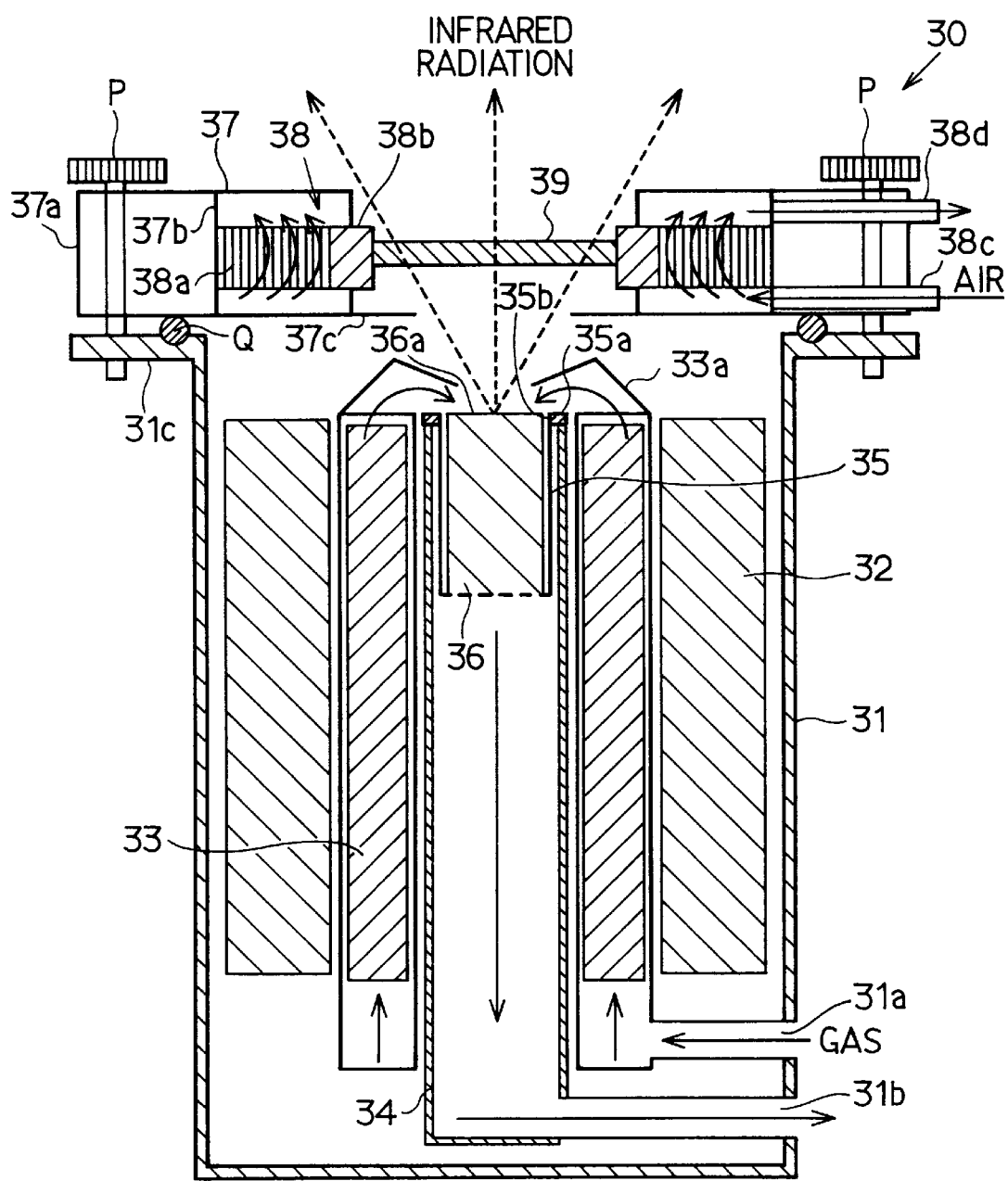
FIG. 3 is a cross-sectional view showing a reaction chamber used in the detecting apparatus according to the present invention.

Referring to FIGS. 1, 2 and 3, an embodiment according to the present invention will be described. FIG. 1 shows a whole system for detecting and analyzing adsorbates on a solid object. The system is composed of a gas supplying device G, an adsorbate detection apparatus S and a gas leakage alarming device A. The gas supplying device G includes gas containers Ga, Gb, Gc and Gd which supply CO, NO, $O_2$ and $H_2$ gasses, respectively, together with a carrier gas to a gas flow rate controller 10. In this particular embodiment, these test gases are used to simulate an exhaust gas from an internal combustion engine. The gases supplied from the containers flow through on-off valves 11a, 11b, 11c and 11d, and mass flow controllers 12a, 12b, 12c and 12d, and are combined into a test gas having a predetermined composition by the mass flow controllers. Then, the test gas is supplied to an adsorbate detection apparatus S. The gas flow rate controller 10 also includes a controller 13 which switches the on-off valves 11a to 11d to an on or off state and also controls the mass flow controllers 12a to 12d so that respective gas flow rates flowing therethrough become required levels. The controller 10 closes the on-off valves 11a to 11d upon receipt of an alarm signal from the gas leakage alarming device A.

As shown in FIGS. 1 and 2, the adsorbate detection device S has a housing 20 in which a reaction chamber 30, an object lens 40 and a gas detector 50 are disposed. The reaction chamber 30 is located on the bottom of the housing 20.

As shown in FIG. 3, the reaction chamber 30 has a cylindrical casing 31 in which a cylindrical furnace 32, a cylindrical passage for heating gas 33, a cylinder 34 and a cylindrical specimen container 35 are disposed coaxially with one another. The gas heating passage 33 and the container 35 are heated by the furnace 32 up to about 1000° C. The gas heating passage is composed of silicon carbide balls (for example, "C-850" made by Ibiden having a diameter of 3 to 5 mm) contained in a case, through which the test gas flows. The test gas supplied from the gas flow rate controller 10 enters into the gas heating passage 33 from an inlet port 31a, flows therethrough, and flows out from the top portion of the passage 33. Then, the test gas is guided by a guide plate 33a disposed on the top of the passage and supplied to the specimen container 35 in which a solid object 36 having through-passages therein and carrying catalyzer materials thereon is contained, and flows through the solid object 36 and flows out from holes made on a bottom wall of the container 35. The test gas further flows through the cylinder 34 and is discharged from an outlet port 31b. The gas discharged from the outlet port 31b is supplied to the gas analyzer which analyzes the composition of the discharged gas. On the inner surface of the guide plate 33a where the test gas is guided, a gold coating having a thickness of 0.5~1.0 μm is formed. The specimen container 35 is supported on the top of the cylinder 34 at its upper flange 35a. The upper surface 36a of the solid object 36 carrying catalyzer thereon is exposed upwardly through an opening of the guide plate 33a, so that infrared radiations from the solid object 36 can be radiated upwardly as shown by dotted lines in FIG. 3. When the test gas flows into the solid object 36, some components contained in the test gas are adsorbed on the upper surface 36a as adsorbates.

A cover assembly is mounted on a casing flange 31c made at an upper portion of the casing 31 and hermetically fixed to the housing 31 by screws P with an O-ring Q interposed therebetween. The cover assembly is composed of a holder 37 having a heat reflector 37c, a cooling device 38 including a window holder 38b and an infrared-transmissive window 39. The heat reflector 37c has a circular opening which is disposed coaxially with the opening of the guide plate 33a so that radiations from the solid object 36 can be radiated therethrough. The heat reflector 37c interrupts heat radiation from the furnace 32 in cooperation with the guide plate 33a to protect the cooling device 38 and the infrared-transmissive window 39 from the heat radiation. On the lower surface of the heat reflector 37c facing the furnace 32, a gold coating is formed as on the inner surface of the guide plate 33a.

Inside the holder 37 there are disposed the cooling device 38 composed of a circular cooling body 38a consisting of a number of aluminum cooling fins and the window holder 38b which is disposed in contact with the cooling body 38a. The circular cooling body 38a is connected to and mounted on a circular wall 37b of the holder 37 at its outer periphery. The cooling body 38a is cooled off by air introduced to the holder 37 from an air inlet port 38c formed on an outer peripheral wall 37a of the holder 37. The air which has cooled off the cooling body 38a is discharged from an air outlet port 38d formed on the wall 37a. The window holder 38b made of a heat conductive material such as a metal is disposed on an inner periphery of the cooling body 38a in contact therewith, and holds the infrared-transmissive window 39 at its center opening. The window holder 38b takes heat away from the window 39 and is cooled off by the cooling body 38a, thereby cooling the window 39 at a temperature lower than 200° C. even when the solid object 36 is heated up to 1000° C.

The infrared-transmissive window 39 is made of an infrared-transmissive material such as zinc sulfide (ZnS), zinc selenide (ZnSe) or the like, and hermetically mounted on the inner periphery of the holder 38b. The window 39 is disposed coaxially with the center opening of the guide plate 33a so that infrared radiations from the solid object 36 are radiated upwardly through the window 39. A closed chamber constituting the reaction chamber 30 is formed by the casing 31 and the cover assembly mounted on the casing with the O-ring Q.

As shown in FIG. 2, an object lens 40 for receiving the infrared radiations radiated through the window 39 and for converging and transmitting the same to an analyzer 60 is disposed at the upper center of the housing 20 coaxially with the window 39. A gas detector 50, such as a diffusion-type detector, is also disposed in the space defined by the housing 20, and detects a gas concentration change in the space which may happen due to a possible breakage of the window 39 or some other causes. When carbon monoxide (CO) gas is used as the test gas, a diffusion-type gas detector such as "KS-20" made by Shin-Cosmos-Denki may be used. Any suitable gas detector may be chosen according to kinds of the test gas. On the top of the housing an adsorbate analyzer 60 is disposed. As the analyzer 60, a Fourier transform infrared emission spectrometer which has a temperature measuring function may be suitable for analyzing adsorbates on an object having a constant temperature. A Fourier transform infrared spectrometer with diffuse reflectance equipment may be used for observing and analyzing surfaces of powder objects. Some other spectrometers which are able to analyze adsorbates in a radiation method such as an infrared spectrometer, Raman spectrometer, Fourier transform Raman spectrometer, or the like may be also used. The spectrometer 60 analyzes the infrared radiations received from the object lens 40 into a spectrum through its optical system 61.

A microscope 70 having an optical system 71 and a pair of binoculars 72 is disposed on the analyzer 60, as shown in FIG. 2. Results of analyses by the analyzer 60 are observed through the binoculars 72. The adsorbate detection apparatus S also includes a data processing unit (not shown in the drawings) which includes a micro-processor and functions of a sequencer and a data buffer. The data processing unit not only collects analyzed data on real time including spectra of adsorbates on the solid object 36 by operating the analyzer 60 and the microscope 70, but also controls the heating temperature of the furnace 32. The collected data are also processed in the data processing unit into adequate forms to be displayed on a cathode ray tube or other display units or to be printed out.

A gas leakage alarming device A is also included in the system as shown in FIG. 1. The alarming device A includes an indicating unit 80a and a alarming unit 80b. The unit 80a sends information to the unit 80b when the former receives such information from the gas detector 50 that a gas leakage has occurred in the housing 20. The alarming unit 80b sends a signal to close the on-off valves 11a~11d to the controller 13 of the gas flow rate controller 10, and the controller 13 in turn shuts down the valves. Thus, gas supply to the mass flow controllers 12a~12d is automatically cut off when gas leakage occurs in the space in the housing 20.

As described above, because the infrared-transmissive window 39 is cooled down by the cooling device 38, influence of the heat from the heating furnace 32 upon the window 39 can be suppressed. Therefore, the adsorbates on solid object 36 can be detected and analyzed through the infrared radiations therefrom under a wide temperature range from a room temperature to a temperature of about 1000° C. This also enables to evaluate the solid object 36 precisely. In addition, the testing operation can be performed safely because the test gas supply is automatically shut down if the test gas leaks in the space defined by the housing 20 by the operation of the gas leakage alarming device A.

Figure 4:
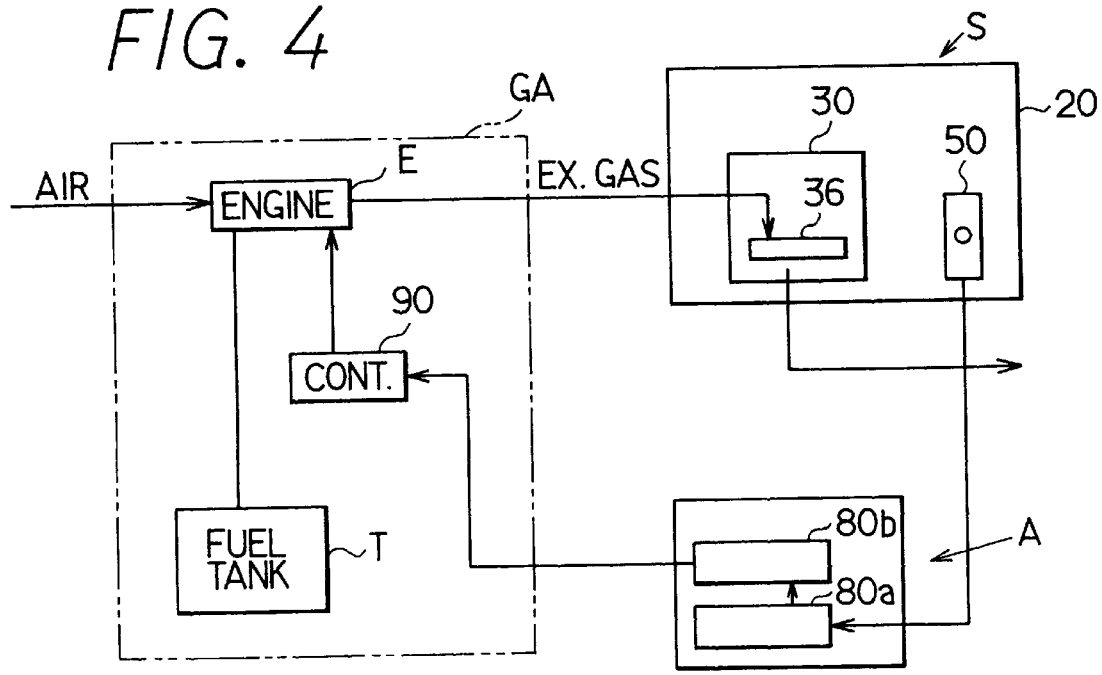
FIG. 4 shows a system modified from the system shown in FIG. 1 according to the present invention.

FIG. 4 show a modification of the embodiment according to the present invention. In this modification, a gas supplying device GA is used in place of the gas supplying device G of the embodiment described above. The gas supplying device GA is composed of an internal combustion engine E, a fuel tank T and a controller 90. The gas supplying device GA supplies exhaust gas from the engine E to the reaction chamber 30 as a test gas. The adsorbate detection apparatus S detects and analyzes the adsorbates adsorbed on the solid object 36 under the actual exhaust gas flow from the engine in the same manner as in the embodiment afore-mentioned. The solid object 36 carrying catalyzer thereon can be evaluated precisely, and its durability can also be evaluated at the same time. Fuel such as gasoline or kerosene is supplied to the internal combustion engine E from the fuel tank T under the control of the controller 90. The controller 90 sets and varies operating conditions of the engine so that the engine is operated, for example, under a fuel rich, stoichiometric or lean condition. The composition of the exhaust gas to be supplied to the reaction chamber 30 varies according to the operating conditions of the engine.

Though the aluminum fins are used as a heat sink in the cooling body 38a, it can be replaced by any other suitable materials which are able to enlarge the surface area contacting a coolant such as air to cool down the infrared-transmissive window 39. Also, the shape of the fins can be chosen variably according to design needs. As the cooling device 38 an electronic cooling device may also be used. Though room temperature air is used as the coolant in the foregoing embodiment, any other fluids of any temperature which are suitable to cool down the cooling body can be used as the coolant as far as the fluids do not give excessive cooling energy to the window 39. The material of the window 39 is not limited to the materials mentioned above, but it may be other materials which have a sufficient transmissivity of infrared radiations and heat resistivity. It is not necessary to dispose the cooling device 38 as a single body with the window 39. The cooling body 38 may be mounted separately from the window 39 as far as it effectively cools down the window 39. Further, it may not be necessary to close the on-off valves automatically when gas leakage occurs, but the valves may be closed manually in case some other safety measures such as alarming are taken.

While the present invention has been shown and described with reference to the foregoing preferred embodiment, it will be apparent to those skilled in the art that changes in form and detail may be made therein without departing from the scope of the invention as defined in the appended claims.

What is claimed is:

1. An apparatus for detecting and analyzing adsorbates adsorbed on a solid object, the apparatus comprising:
    a closed reaction chamber for containing the solid object therein and forming adsorbates on the solid object under an elevated temperature by supplying test gases thereinto;
    a heating device, disposed in the closed reaction chamber for heating the solid object and the test gases;
    an infrared-transmissive window hermetically held on the closed reaction chamber so that the infrared radiation from the adsorbates is radiated through the infrared-transmissive window;
    a cooling device for cooling the infrared-transmissive window;
    a heat interruption member, disposed in the closed reaction chamber, for interrupting heat radiated from the heating device to the cooling device; and
    optical means, operably connected to the closed reaction chamber, for detecting and analyzing the adsorbates adsorbed on the solid object based on the infrared radiation radiated from the adsorbates through the infrared-transmissive window.

2. The apparatus for detecting and analyzing adsorbates as in claim 1, wherein:
    the heat interruption member includes a guide plate which covers a top surface of the heating device and interrupts heat radiation from the heating device to the cooling device.

3. The apparatus for detecting and analyzing adsorbates as in claim 2, wherein:
    the heat interruption member further includes a heat reflector which is disposed under the cooling device and reflects heat radiation from the heating device.

4. The apparatus for detecting and analyzing adsorbates as in claim 1, further comprising:
    a gas detector for detecting gases leaked from the closed reaction chamber; and
    a gas leakage alarming device for generating a gas leakage alarm upon receipt of a signal from the gas detector.

5. The apparatus for detecting and analyzing adsorbates as in claim 1, wherein:
    the cooling device includes a window holder for hermetically holding the infrared-transmissive window and adsorbing heat therefrom and a cooling body disposed in contact with the window holder for cooling the window holder; and the cooling body has a number of aluminum cooling fins which are cooled by outside air taken into the cooling device.

6. The apparatus for detecting and analyzing adsorbates as in claim 1, wherein:

the heating device comprises a cylindrical gas passage disposed around the solid object and a cylindrical furnace disposed around the cylindrical gas passage; and the solid object and the test gases flowing through the cylindrical gas passage are heated by the cylindrical furnace.

7. An apparatus for detecting and analyzing adsorbates adsorbed on a solid object, the apparatus comprising:

a closed reaction chamber for containing the solid object therein and forming adsorbates on the solid object under an elevated temperature by supplying test gases thereinto;

a heating device, disposed in the closed reaction chamber for heating the solid object and the test gases;

an infrared-transmissive window formed in a wall of the closed reaction chamber so that infrared radiation from the adsorbates is radiated through the infrared-transmissive window;

a cooling device for cooling the infrared-transmissive window;

a heat interruption member, disposed in the closed reaction chamber, for interrupting heat radiated from the heating device to the infrared-transmissive window; and an infrared radiation detecting device for detecting and analyzing the adsorbates adsorbed on the solid object based on the infrared radiation radiated from the adsorbates through the infrared-transmissive window.

8. The apparatus for detecting and analyzing adsorbates as in claim 7, wherein:

the heat interruption member includes a guide plate which covers a top surface of the heating device and interrupts heat radiation from the heating device to the infrared-transmissive window.

9. The apparatus for detecting and analyzing adsorbates as in claim 8, wherein:

the heat interruption member further includes a heat reflector which is disposed adjacent a portion of the infrared-transmissive window and reflects heat radiation from the heating device.

* * * * *